(12) United States Patent
Howard

(10) Patent No.: US 11,806,547 B2
(45) Date of Patent: Nov. 7, 2023

(54) STIMULATION SYSTEMS WITH A LENS ARRANGEMENT FOR LIGHT COUPLING AND METHODS OF MAKING AND USING

(71) Applicant: Boston Scientific Neuromodulation Corporation, Valencia, CA (US)

(72) Inventor: Joshua Dale Howard, Sacramento, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 150 days.

(21) Appl. No.: 17/463,206

(22) Filed: Aug. 31, 2021

(65) Prior Publication Data
US 2022/0072329 A1    Mar. 10, 2022

Related U.S. Application Data

(60) Provisional application No. 63/074,590, filed on Sep. 4, 2020.

(51) Int. Cl.
*A61N 5/06*    (2006.01)
*F21V 5/04*    (2006.01)
*F21W 131/20*    (2006.01)

(52) U.S. Cl.
CPC .............. *A61N 5/0601* (2013.01); *F21V 5/041* (2013.01); *A61N 2005/063* (2013.01);
(Continued)

(58) Field of Classification Search
CPC .......... A61N 5/0601; A61N 2005/0626; A61N 2005/063; F21V 5/041; F21V 2200/10; F21W 2131/20; G02B 6/4206
See application file for complete search history.

(56) References Cited

U.S. PATENT DOCUMENTS

| 4,920,979 A | 5/1990 | Bullara |
| 5,076,270 A | 12/1991 | Stutz, Jr. |

(Continued)

FOREIGN PATENT DOCUMENTS

| WO | 02/091935 | 11/2002 |
| WO | 2011/031131 | 3/2011 |

(Continued)

OTHER PUBLICATIONS

Robert Gale Wilson, "Ball-lens coupling efficiency for laser-diode to single-mode fiber: comparison of independent studies by distinct methods," Appl. Opt. 37, 3201-3205 (1998) (Year: 1998).*

(Continued)

*Primary Examiner* — Brian T Gedeon
*Assistant Examiner* — Joshua Andrew Schum-Houck
(74) *Attorney, Agent, or Firm* — Branch Partners PLLC; Bruce E. Black

(57) ABSTRACT

An implantable light generation arrangement for an optical or optical/electrical stimulation system includes a light source having an emission surface, wherein the light source is configured to generate light and emit the light from the emission surface; an optical waveguide having a first end and a core; a ball lens disposed between the light source and the optical waveguide and configured to receive the light emitted from the light source and direct the light onto the core at the first end of the optical waveguide; and a fixture holding the light source, optical waveguide, and ball lens in a fixed arrangement.

20 Claims, 8 Drawing Sheets

(52) U.S. Cl.
CPC ... *A61N 2005/0626* (2013.01); *F21V 2200/10* (2015.01); *F21W 2131/20* (2013.01)

(56) References Cited

U.S. PATENT DOCUMENTS

| | | | |
|---|---|---|---|
| 5,437,193 A | 8/1995 | Schleitweiler et al. | |
| 5,445,608 A | 8/1995 | Chen et al. | |
| 5,556,421 A | 9/1996 | Prutchi et al. | |
| 5,824,027 A | 10/1998 | Hoffer et al. | |
| 6,175,710 B1 | 1/2001 | Kamaji et al. | |
| 6,181,969 B1 | 1/2001 | Gord | |
| 6,224,450 B1 | 5/2001 | Norton | |
| 6,271,094 B1 | 8/2001 | Boyd et al. | |
| 6,295,944 B1 | 10/2001 | Lovett | |
| 6,364,278 B1 | 4/2002 | Lin et al. | |
| 6,366,719 B1 | 4/2002 | Heath et al. | |
| 6,391,985 B1 | 5/2002 | Goode et al. | |
| 6,442,435 B2 | 8/2002 | King et al. | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,895,280 B2 | 5/2005 | Meadows et al. | |
| 6,988,001 B2 | 1/2006 | Greatbatch et al. | |
| 6,993,384 B2 | 1/2006 | Bradley et al. | |
| 7,190,993 B2 | 3/2007 | Sharma et al. | |
| 7,244,150 B1 | 7/2007 | Brase et al. | |
| 7,252,677 B2 | 8/2007 | Burwell et al. | |
| 7,288,108 B2 | 10/2007 | DiMauro et al. | |
| 7,395,118 B2 | 7/2008 | Erickson | |
| 7,437,193 B2 | 10/2008 | Parramon et al. | |
| 7,450,997 B1 | 11/2008 | Pianca et al. | |
| 7,672,734 B2 | 3/2010 | Anderson et al. | |
| 7,684,869 B2 | 3/2010 | Bradley et al. | |
| 7,736,382 B2 | 6/2010 | Webb et al. | |
| 7,761,165 B1 | 7/2010 | He et al. | |
| 7,783,359 B2 | 8/2010 | Meadows | |
| 7,792,590 B1 | 9/2010 | Pianca et al. | |
| 7,803,021 B1 | 9/2010 | Brase | |
| 7,809,446 B2 | 10/2010 | Meadows | |
| 7,946,980 B2 | 5/2011 | Reddy et al. | |
| 7,949,395 B2 | 5/2011 | Kuzma | |
| 7,949,409 B2 | 5/2011 | Bly et al. | |
| 7,974,706 B2 | 7/2011 | Moffitt et al. | |
| 8,086,322 B2 | 12/2011 | Schouenborg | |
| 8,175,710 B2 | 5/2012 | He | |
| 8,224,450 B2 | 7/2012 | Brase | |
| 8,271,094 B1 | 9/2012 | Moffitt et al. | |
| 8,295,944 B2 | 10/2012 | Howard et al. | |
| 8,311,647 B2 | 11/2012 | Bly | |
| 8,326,433 B2 | 12/2012 | Blum et al. | |
| 8,340,785 B2 | 12/2012 | Bonde et al. | |
| 8,364,278 B2 | 1/2013 | Pianca et al. | |
| 8,386,054 B2 | 2/2013 | North | |
| 8,391,985 B2 | 3/2013 | McDonald | |
| 8,463,343 B2 | 6/2013 | Kuhn et al. | |
| 8,473,061 B2 | 6/2013 | Moffitt et al. | |
| 8,483,237 B2 | 7/2013 | Zimmermann et al. | |
| 8,525,027 B2 | 9/2013 | Lindner et al. | |
| 8,571,665 B2 | 10/2013 | Moffitt et al. | |
| 8,600,509 B2 | 12/2013 | McDonald et al. | |
| 8,675,945 B2 | 3/2014 | Barnhorst et al. | |
| 8,682,439 B2 | 3/2014 | DeRohan et al. | |
| 8,688,235 B1 | 4/2014 | Pianca et al. | |
| 8,792,993 B2 | 7/2014 | Pianca et al. | |
| 8,831,731 B2 | 9/2014 | Blum et al. | |
| 8,831,742 B2 | 9/2014 | Pianca et al. | |
| 8,831,746 B2 | 9/2014 | Swanson | |
| 8,849,632 B2 | 9/2014 | Sparks et al. | |
| 8,868,211 B2 | 10/2014 | Durand et al. | |
| 8,897,876 B2 | 11/2014 | Sundaramurthy et al. | |
| 8,929,973 B1 | 1/2015 | Webb et al. | |
| 8,936,630 B2 | 1/2015 | Denison et al. | |
| 8,958,615 B2 | 2/2015 | Blum et al. | |
| 9,238,132 B2 | 1/2016 | Barker | |
| 9,409,032 B2 | 8/2016 | Brase et al. | |
| 9,415,154 B2 | 8/2016 | Leven | |
| 9,421,362 B2 | 8/2016 | Seeley | |
| 9,440,066 B2 | 9/2016 | Black | |
| 9,550,063 B2 | 1/2017 | Wolf, II | |
| 9,604,068 B2 | 3/2017 | Malinowski | |
| 9,643,010 B2 | 5/2017 | Ranu | |
| 9,656,093 B2 | 5/2017 | Villarta et al. | |
| 9,681,809 B2 | 6/2017 | Sharma et al. | |
| 9,770,598 B2 | 9/2017 | Malinowski et al. | |
| 9,931,511 B2 | 4/2018 | Kaula et al. | |
| 10,307,602 B2 | 6/2019 | Leven | |
| 10,471,273 B2 | 11/2019 | Segev et al. | |
| 2002/0156513 A1 | 10/2002 | Borkan | |
| 2002/0161417 A1 | 10/2002 | Scribner | |
| 2004/0098063 A1 | 5/2004 | Goetz | |
| 2004/0147964 A1 | 7/2004 | Nolan et al. | |
| 2005/0216072 A1 | 9/2005 | Mahadevan-Jansen et al. | |
| 2006/0129210 A1 | 6/2006 | Cantin et al. | |
| 2006/0155348 A1 | 7/2006 | deCharms | |
| 2006/0161227 A1 | 7/2006 | Walsh, Jr. et al. | |
| 2007/0053996 A1 | 3/2007 | Boyden et al. | |
| 2007/0100398 A1 | 5/2007 | Sloan | |
| 2007/0150036 A1 | 6/2007 | Anderson | |
| 2007/0161919 A1 | 7/2007 | DiLorenzo | |
| 2007/0244526 A1 | 10/2007 | Zaghetto et al. | |
| 2008/0046053 A1 | 2/2008 | Wagner et al. | |
| 2008/0077198 A1 | 3/2008 | Webb et al. | |
| 2008/0146890 A1 | 6/2008 | LeBouef et al. | |
| 2008/0167701 A1 | 7/2008 | John et al. | |
| 2008/0197300 A1 | 8/2008 | Kayser et al. | |
| 2008/0243218 A1 | 10/2008 | Bottomley et al. | |
| 2009/0054954 A1 | 2/2009 | Foley et al. | |
| 2009/0054955 A1 | 2/2009 | Kopell et al. | |
| 2009/0069871 A1 | 3/2009 | Mahadevan-Jansen et al. | |
| 2009/0118800 A1 | 5/2009 | Deisseroth et al. | |
| 2009/0187222 A1 | 7/2009 | Barker | |
| 2009/0196471 A1 | 8/2009 | Goetz et al. | |
| 2009/0276021 A1 | 11/2009 | Meadows et al. | |
| 2009/0287272 A1 | 11/2009 | Kokones et al. | |
| 2009/0287273 A1 | 11/2009 | Carlton et al. | |
| 2009/0299447 A1 | 12/2009 | Jensen et al. | |
| 2010/0076508 A1 | 3/2010 | McDonald et al. | |
| 2010/0076535 A1 | 3/2010 | Pianca et al. | |
| 2010/0094364 A1 | 4/2010 | McDonald | |
| 2010/0105997 A1 | 4/2010 | Ecker et al. | |
| 2010/0114190 A1 | 5/2010 | Bendett et al. | |
| 2010/0174329 A1 | 7/2010 | Dadd et al. | |
| 2010/0174344 A1 | 7/2010 | Dadd et al. | |
| 2010/0256693 A1 | 10/2010 | McDonald et al. | |
| 2010/0268298 A1 | 10/2010 | Moffitt et al. | |
| 2010/0292758 A1 | 11/2010 | Lee et al. | |
| 2010/0324630 A1 | 12/2010 | Lee et al. | |
| 2010/0326701 A1 | 12/2010 | McDonald | |
| 2011/0004267 A1 | 1/2011 | Meadows | |
| 2011/0005069 A1 | 1/2011 | Pianca | |
| 2011/0009932 A1 | 1/2011 | McDonald et al. | |
| 2011/0022100 A1 | 1/2011 | Brase et al. | |
| 2011/0029055 A1 | 2/2011 | Tidemand | |
| 2011/0046432 A1 | 2/2011 | Simon et al. | |
| 2011/0046700 A1 | 2/2011 | McDonald et al. | |
| 2011/0078900 A1 | 4/2011 | Pianca et al. | |
| 2011/0106208 A1 | 5/2011 | Faltys et al. | |
| 2011/0112591 A1* | 5/2011 | Seymour | A61B 5/4076 600/377 |
| 2011/0125077 A1 | 5/2011 | Denison et al. | |
| 2011/0125078 A1 | 5/2011 | Denison et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0172653 A1 | 7/2011 | Schneider et al. | |
| 2011/0172725 A1 | 7/2011 | Wells et al. | |
| 2011/0238129 A1 | 9/2011 | Moffitt et al. | |
| 2011/0295331 A1 | 12/2011 | Wells et al. | |
| 2011/0313500 A1 | 12/2011 | Barker et al. | |
| 2012/0014580 A1 | 1/2012 | Blum et al. | |
| 2012/0016378 A1 | 1/2012 | Pianca et al. | |
| 2012/0046710 A1 | 2/2012 | Digiore et al. | |

(56) References Cited

U.S. PATENT DOCUMENTS

| | | |
|---|---|---|
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0232354 A1 | 9/2012 | Ecker et al. |
| 2012/0253261 A1 | 10/2012 | Poletto et al. |
| 2012/0265262 A1 | 10/2012 | Osorio |
| 2012/0265268 A1 | 10/2012 | Blum et al. |
| 2012/0287420 A1 | 11/2012 | McLaughlin et al. |
| 2012/0314924 A1 | 12/2012 | Carlton et al. |
| 2012/0316615 A1 | 12/2012 | Digiore et al. |
| 2013/0019325 A1 | 1/2013 | Deisseroth et al. |
| 2013/0053905 A1 | 2/2013 | Wagner |
| 2013/0079848 A1 | 3/2013 | Campbell et al. |
| 2013/0102861 A1 | 4/2013 | Oki et al. |
| 2013/0105071 A1 | 5/2013 | Digiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0281819 A1 | 10/2013 | Schmid |
| 2013/0304152 A1 | 11/2013 | Bradley et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0067015 A1 | 3/2014 | Kothandaraman et al. |
| 2014/0067023 A1 | 3/2014 | Register et al. |
| 2014/0074182 A1 | 3/2014 | Wolf, II |
| 2014/0114150 A1 | 4/2014 | Pogue et al. |
| 2014/0122379 A1 | 5/2014 | Moffitt et al. |
| 2014/0142664 A1 | 5/2014 | Roukes et al. |
| 2014/0148753 A1* | 5/2014 | Leven ............... A61N 1/0551 604/21 |
| 2014/0163639 A1 | 6/2014 | Zhu |
| 2014/0200639 A1 | 7/2014 | De La Rama |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0005860 A1 | 1/2015 | Howard et al. |
| 2015/0018915 A1 | 1/2015 | Leven |
| 2015/0021817 A1 | 1/2015 | Romero et al. |
| 2015/0045862 A1 | 2/2015 | Goldman et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2015/0202456 A1 | 7/2015 | Andersen et al. |
| 2015/0290461 A1 | 10/2015 | Min et al. |
| 2015/0306414 A1 | 10/2015 | Nielsen et al. |
| 2015/0360031 A1 | 12/2015 | Bornzin et al. |
| 2015/0375006 A1 | 12/2015 | Denison et al. |
| 2016/0030749 A1 | 2/2016 | Carcieri et al. |
| 2016/0045740 A1 | 2/2016 | Rezai et al. |
| 2016/0082251 A1 | 3/2016 | Moffitt et al. |
| 2016/0082253 A1 | 3/2016 | Moffitt et al. |
| 2016/0228692 A1 | 8/2016 | Steinke et al. |
| 2016/0250474 A1 | 9/2016 | Stack et al. |
| 2016/0256689 A1 | 9/2016 | Vallejo et al. |
| 2016/0271392 A1 | 9/2016 | Vallejo et al. |
| 2016/0271413 A1 | 9/2016 | Vallejo et al. |
| 2016/0287885 A1 | 10/2016 | Saini |
| 2016/0296745 A1 | 10/2016 | Govea et al. |
| 2016/0346557 A1 | 12/2016 | Bokil |
| 2016/0361543 A1 | 12/2016 | Kaula et al. |
| 2016/0367836 A1* | 12/2016 | Kampasi ............... G02B 6/0008 |
| 2016/0375258 A1 | 12/2016 | Steinke |
| 2017/0061627 A1 | 3/2017 | Bokil |
| 2017/0095670 A1 | 4/2017 | Ghaffari et al. |
| 2017/0100580 A1 | 4/2017 | Olson |
| 2017/0136254 A1 | 5/2017 | Simon et al. |
| 2017/0225007 A1 | 8/2017 | Orinski |
| 2017/0259078 A1 | 9/2017 | Howard |
| 2017/0281966 A1 | 10/2017 | Basiony |
| 2017/0304633 A1 | 10/2017 | Zhang |
| 2017/0348522 A1 | 12/2017 | Stoffregen et al. |
| 2017/0361108 A1 | 12/2017 | Leven |
| 2017/0361122 A1 | 12/2017 | Chabrol et al. |
| 2018/0028820 A1 | 2/2018 | Nageri |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0110971 A1 | 4/2018 | Serrano Carmona |
| 2018/0154152 A1 | 6/2018 | Chabrol et al. |
| 2018/0193655 A1 | 7/2018 | Zhang et al. |
| 2018/0229042 A1 | 8/2018 | Kaula et al. |
| 2018/0243570 A1 | 8/2018 | Malinowski et al. |
| 2018/0256906 A1 | 9/2018 | Pivonka et al. |
| 2018/0318578 A1 | 11/2018 | Ng et al. |
| 2018/0326219 A1 | 11/2018 | Wolf, II |
| 2018/0369606 A1 | 12/2018 | Zhang et al. |
| 2018/0369607 A1 | 12/2018 | Zhang et al. |
| 2018/0369608 A1 | 12/2018 | Chabrol |
| 2019/0209834 A1 | 7/2019 | Zhang et al. |
| 2019/0209849 A1 | 7/2019 | Hershey et al. |
| 2020/0094047 A1 | 3/2020 | Govea et al. |
| 2020/0155854 A1 | 5/2020 | Leven et al. |
| 2020/0271796 A1 | 8/2020 | Tahon et al. |
| 2020/0376262 A1 | 12/2020 | Clark et al. |

FOREIGN PATENT DOCUMENTS

| | | |
|---|---|---|
| WO | 2011150430 | 12/2011 |
| WO | 2012/103543 | 8/2012 |
| WO | 2014143387 | 9/2014 |
| WO | 2019/183054 | 9/2019 |
| WO | 2019/183068 | 9/2019 |
| WO | 2019/183075 | 9/2019 |
| WO | 2019/183078 | 9/2019 |

OTHER PUBLICATIONS

R G Wilson, "Ball-lens coupling efficiency for laser-diode to single-mode fiber: comparison of independent studies by distinct methods," Applied Optics May 20, 1998, 37 (15): 3201-5.

International Search Report and Written Opinion for PCT Application No. PCT/US2021/048519 dated Jan. 11, 2022.

Baxter, G.D. et al., Effects of Low Intensity Infrared Laser Irradiation Upon Conduction in the Human Median Nerve In Vivo, Experimental Physiology (1994) 79, 227-234.

Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.

Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.

Snyder-Mackler, Lynn et al., Effect of Helium-Neon Laser Irradiation on Peripheral Sensory Nerve Latency, Phys. Ther. (1988), 68:223-225.

Darlot, Fannie et al., Near-infrared light is neuroprotective in a monkey model of Parkinson's disease (2006), 30 pages.

Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.

Barnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).

(56) References Cited

OTHER PUBLICATIONS

Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.

Use of NAD(P)H and flavoprotein autofluorescence transients to probe neuron and astrocyte responses to synaptic activation. Shuttleworth 2010 Neurochemestry international.

Vallejo, Ricardo, Kerry Bradley, and Leonardo Kapural. "Spinal cord stimulation in chronic pain: Mode of action." Spine 42 (2017): S53-S60.

Vivianne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.

* cited by examiner

STIMULATION SYSTEMS WITH A LENS ARRANGEMENT FOR LIGHT COUPLING AND METHODS OF MAKING AND USING

CROSS-REFERENCE TO RELATED APPLICATIONS

This application claims the benefit under 35 U.S.C. § 119(e) of U.S. Provisional Patent Application Ser. No. 63/074,590, filed Sep. 4, 2020, which is incorporated herein by reference.

FIELD

The present disclosure is directed to the area of implantable optical or optical/electrical stimulation systems and methods of making and using the systems. The present disclosure is also directed to implantable optical or optical/electrical stimulation systems that include a lens arrangement for coupling light into an optical waveguide and methods of making and using.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Optical stimulation can also provide therapeutic benefits in a variety of diseases and disorders by itself or in combination with electrical stimulation. An optical stimulation system may include a stimulator with one or more light sources and, often, one or more optical fibers to carry the light to the desired stimulation site.

BRIEF SUMMARY

In one aspect, an implantable light generation arrangement for an optical or optical/electrical stimulation system includes a light source having an emission surface, wherein the light source is configured to generate light and emit the light from the emission surface; an optical waveguide having a first end and a core; a ball lens disposed between the light source and the optical waveguide and configured to receive the light emitted from the light source and direct the light onto the core at the first end of the optical waveguide, wherein the ball lens is spaced apart from both the emission surface of the light source and the first end of the optical waveguide; and a fixture holding the light source, optical waveguide, and ball lens in a fixed arrangement.

In another aspect, an implantable light generation arrangement for an optical or optical/electrical stimulation system includes a light source having an emission surface, wherein the light source is configured to generate light and emit the light from the emission surface; an optical waveguide having a first end and a core; a ball lens disposed between the light source and the optical waveguide and configured to receive the light emitted from the light source and direct the light onto the core at the first end of the optical waveguide; a fixture holding the light source, optical waveguide, and ball lens in a fixed arrangement; and a lead including terminals disposed along a proximal end of the lead and conductors coupled to the terminals and extending along the lead, wherein at least two of the conductors are coupled to the light source to electrically couple the light source to at least two of the terminals.

In a further aspect, an implantable light generation arrangement for an optical or optical/electrical stimulation system includes a light source having an emission surface, wherein the light source is configured to generate light and emit the light from the emission surface; an optical waveguide having a first end and a core; a ball lens disposed between the light source and the optical waveguide and configured to receive the light emitted from the light source and direct the light onto the core at the first end of the optical waveguide, wherein the ball lens has a diameter that is at least twice as large as a diameter of the emission surface of the light source; and a fixture holding the light source, optical waveguide, and ball lens in a fixed arrangement.

In at least some aspects, the implantable light generation arrangement further includes a lead including terminals disposed along a proximal end of the lead and conductors coupled to the terminals and extending along the lead, wherein at least two of the conductors are coupled to the light source to electrically couple the light source to at least two of the terminals.

In at least some aspects, the implantable light generation arrangement further includes a casing surrounding the light source, a portion of the optical waveguide, the ball lens, and the fixture. In at least some aspects, another portion of the optical waveguide and at least a portion of the lead extend out of the casing.

In at least some aspects, the ball lens has a diameter that is at least five times as large as a diameter of the core of the optical waveguide. In at least some aspects, the first end of the optical waveguide is spaced apart from the ball lens by a distance of at least 0.5 mm. In at least some aspects, the emission surface of the light source is spaced apart from the ball lens by a distance of at least 0.1 mm. In at least some aspects, the ball lens has a diameter of at least 4 mm.

In at least some aspects, the implantable light generation arrangement further includes a distal lead including electrodes disposed along a distal end of the distal lead, wherein a portion of the optical waveguide extends along the distal lead.

In yet another aspect, a system for an optical or optical/electrical stimulation includes any of the implantable light generation arrangement described above and a control module electrically coupleable to the light source of the light generation arrangement. In at least some aspects, the control module is programmable.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of implantable optical or optical/electrical stimulation systems and methods of making and using the systems. The present disclosure is also directed to implantable optical or optical/electrical stimulation systems that include a lens arrangement for coupling light into an optical waveguide and methods of making and using.

The stimulation systems described herein can produce optical or both optical and electrical stimulation. In at least some of these embodiments, the optical stimulation can be provided through a modification of an electrical stimulation system. Optical stimulation may include, but is not necessarily limited to, stimulation resulting from response to particular wavelengths or wavelength ranges of light or from thermal effects generated using light or any combination thereof.

An implantable optical or optical/electrical stimulation system includes a light source, such as a light emitting diode (LED), laser diode, a vertical cavity side-emitting laser (VCSEL), an organic light emitting diode (OLED), a lamp, or any other suitable light source. A challenge for such systems is the coupling of the light from the light source into an optical waveguide, such as an optical fiber, to deliver the light to the stimulation site. As one example, the core of an optical fiber may be approximately 0.1 to 1 mm in diameter. Alignment of the light source with this core can be challenging. Many conventional arrangements for such light coupling are difficult to fit into the small space afforded for an implantable stimulation system.

Figure 1A:
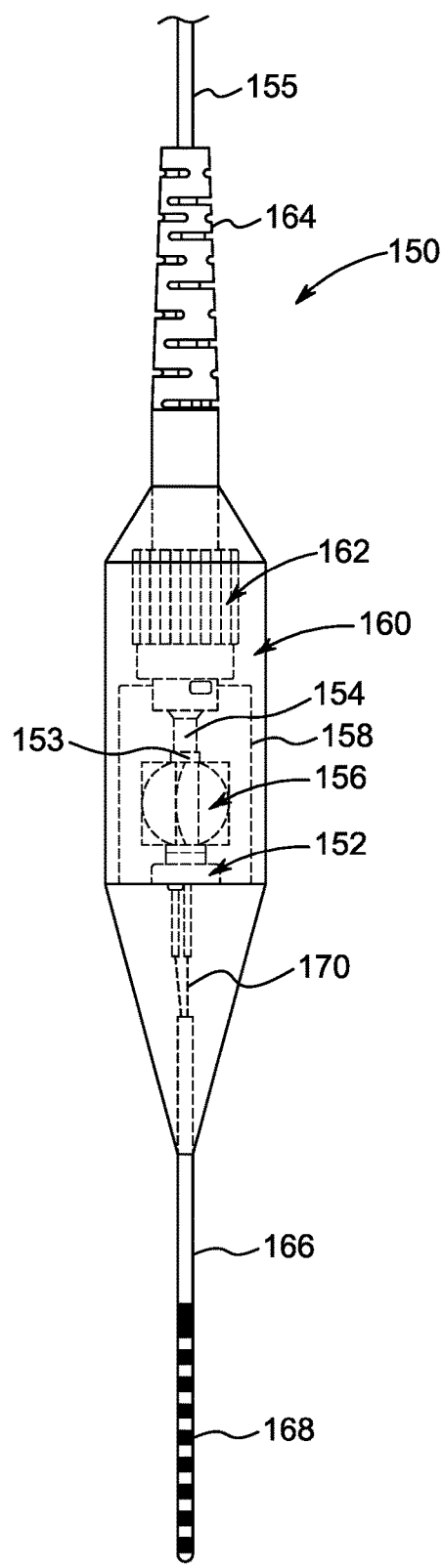
FIG. 1A is a schematic side view of one embodiment of an implantable light generation arrangement.

FIG. 1A illustrates one embodiment of an implantable arrangement 150 (i.e., an implantable light generation arrangement) for coupling light from a light source 152 into a core 153 of an optical waveguide 154 using a lens 156. In the illustrated embodiment, the lens 156 is a ball lens. It will be understood that other lenses can be used including other biconvex lenses. In the illustrated embodiment, the optical waveguide 154 is an optical fiber with a core 153 and a cladding 155, although any other suitable optical waveguide can be used.

A ball lens is a spherical lens and can be readily manufactured with a diameter of at least 0.5, 1, 2, 3, 4, or 5 mm or in the range of 0.5 to 10 mm (or more) or in the range of 2 to 8 mm. In at least some embodiments, the lens 156 is a ball lens made of a solid material. In other embodiments, the lens 156 is a ball lens made of solid shell with a liquid material within the shell. In at least some embodiments, the lens 156 is made of a material having an index of refraction in a range of 1.3 to 1.7 or in a range of 1.4 to 1.6, although in other embodiments materials with an index of refraction outside these ranges can be used.

In at least some embodiments, the lens 156 is selected so that the effective focal length of the lens is no more than 5, 4, 3, 2, 1, or 0.5 mm or less from the lens. In at least some embodiments, the lens 156 is spaced apart from the end of the core 153 of the optical waveguide 154. In at least some embodiments, the lens 156 is spaced apart from the emission surface 151 of the light source 152.

Figure 1B:
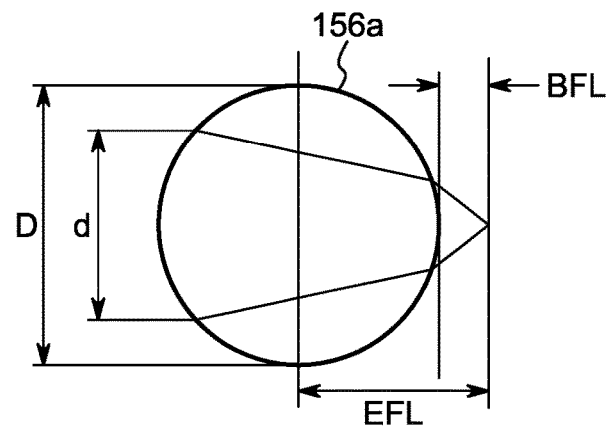
FIG. 1B is a schematic side view of one embodiment of a ball lens and parameters associated with the ball lens.

FIG. 1B illustrates a ball lens 156a and indicates the diameter, D, of the ball lens; the diameter, d, of the emission surface 151 of the light source 152; the effective focal length, EFL, of the ball lens; and the back focal length, BFL, of the ball lens. The following equations use the two diameters, D and d, as well as the index of refraction, n, of the ball lens material to calculate the EFL, BFL, and numerical aperture, NA, of the ball lens (assuming for NA that the light from the light source is collimated).

$$EFL = \frac{nD}{4(n-1)}$$

$$BFL = EFL - \frac{D}{2}$$

$$NA = \frac{1}{\sqrt{1 + 4\left(\frac{nD}{4d(n-1)}\right)^2}}$$

Figure 1C:
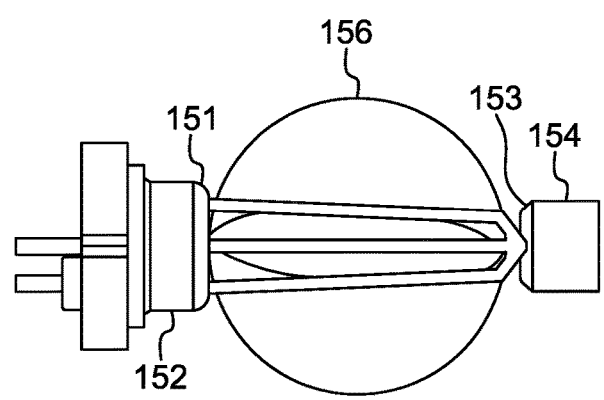
FIG. 1C is a schematic side view of one embodiment of a light source, ball lens, and optical waveguide.

In at least some embodiments, the NA of the lens 156 is the same or smaller than the numerical aperture of the optical waveguide 154. The ball lens 156a facilitates coupling light from the light source 152 to the optical waveguide 154, as illustrated in FIG. 1C, by selecting or adjusting the NA of the ball lens 156a using either, or both, the selection or adjustment of the diameter, D, of the ball lens or the index of refraction, n, of the ball lens material (for example, by selecting from different glasses or other materials with different indices of refraction).

In at least some embodiments, the diameter, D, of the ball lens 156a is larger than the diameter, d, of the emission surface 151 of the light source 152. In at least some embodiments, the diameter, d, of the emission surface 151 of the light source 152 is at least 0.5, 0.75, 1, 1.25, 1.5, 2, or 2.5 mm or is in a range of 0.5 to 4 mm or in a range of 0.7 to 2.5 mm. In at least some embodiments, the diameter, D, of the ball lens 156a is at least 2, 3, or 4 or more times the diameter, d, of the emission surface 151 of the light source 152. In at least some embodiments, the ball lens 156a is spaced apart from the emission surface 151 of the light source 152 by, for example, a distance of at least 0.1, 0.2, or 0.25 mm or a distance in a range of 0.1 to 0.5 mm.

In at least some embodiments, the diameter of the core 153 of the optical waveguide 154 is at least 0.05, 0.1, 0.2, 0.5, or 1 mm or is in a range of 0.05 to 2 mm or in a range of 0.1 to 1 mm. In at least some embodiments, the diameter, D, of the ball lens 156a is at least 2, 3, 5, 8, 10, 15, 20 or 25 or more times the diameter of the core 153 of the optical waveguide 154. In at least some embodiments, the diameter, d, of the emission surface 151 of the light source 152 is at least 2, 3, 5, 8, or 10 or more times the diameter of the core 153 of the optical waveguide 154. As an example, in one embodiment the diameter of the core 153 of the optical waveguide 154 is 0.2 mm, the diameter of the emission surface 151 of the light source 152 is 1.6 mm, and the diameter of the ball lens 156a is 6 mm.

In at least some embodiments, the end of the optical waveguide 154 is positioned at or near (for example, within 3, 2, 1, or 0.5 mm or less of) the effective focal length of the lens 156. In at least some embodiments, the end of the optical waveguide 154 and the lens 156 are spaced apart by a distance of at least 0.5, 1, or 1.25 mm or a distance in a range of 0.5 to 5 mm or in a range of 1 to 2.5 mm. As an example, in one embodiment the light source 152 is spaced apart from the ball lens 156a by 0.25 mm and the end of the optical waveguide 154 is spaced apart from the ball lens 156a by 1.4 mm.

Returning to FIG. 1A, a fixture 158 is provided to affix the light source 152, optical waveguide 154, and lens 156 is an aligned position. In at least some embodiments, a casing 160 is disposed (for example, molded or placed) around the fixture 158, light source 152, optical waveguide 154, and lens 156 to provide further stability and, at least in some embodiments, provide hermiticity for the components within the casing. In at least some embodiments, the casing 160 is made of silicone.

Figure 2:
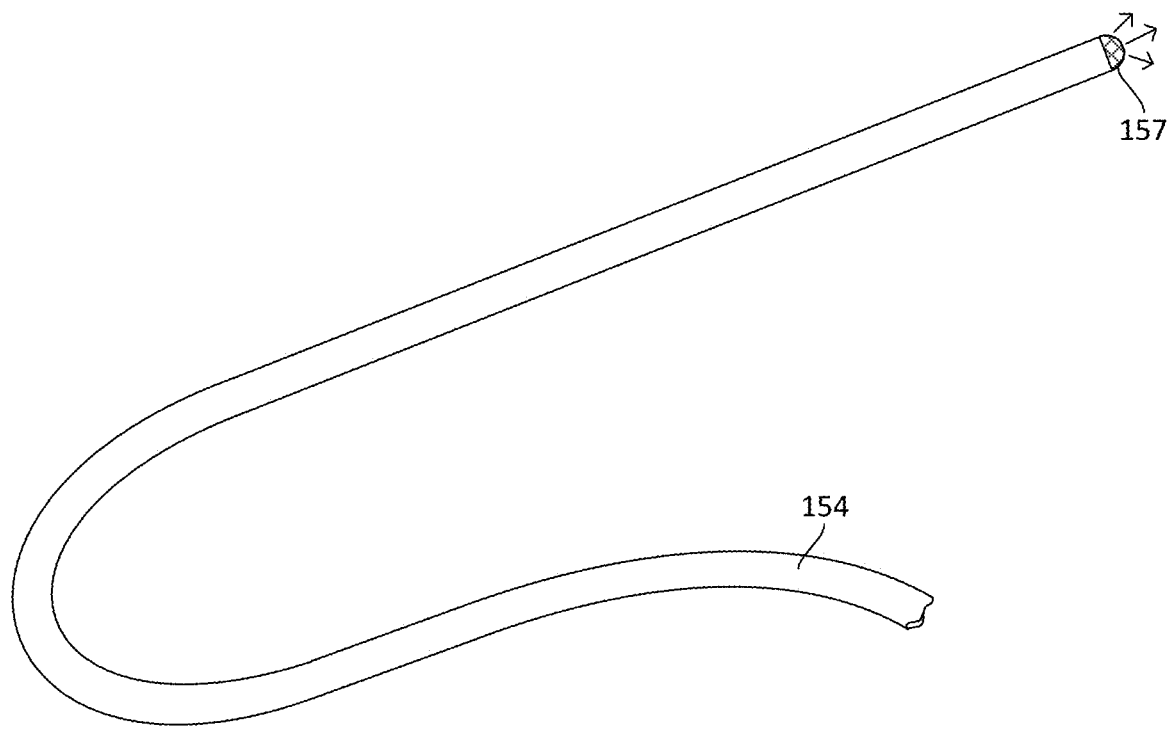
FIG. 2 is a schematic side view of one embodiment of a distal portion of an optical waveguide of the implantable light generation arrangement of FIG. 1A.

In at least some embodiments, the implantable arrangement 150 is coupled to a control module, as illustrated in FIG. 2 and described in more detail below. FIG. 1A illustrates that, in at least some embodiments, the implantable arrangement 150 can include an optical FC/PC connector 162 and strain relief 164 for the optical waveguide 154 (e.g., an optical fiber) exiting the casing 160. In addition, in at least some embodiments, a lead 166 with terminals 168 extends from the casing 160. The lead 166 (or lead extension) includes conductors 170, such as wires, that couple the light source 152 to the terminals 168 of the lead 166. The conductors 170 extend along the lead 166 to the terminals 168. In at least some embodiments, a different conductor 170 extends to each terminal 168 or at least two conductors 170 extend to two different terminals 168. The lead 166 can be coupled to a control module 146, as described below, to drive the light source 152 via the terminals 168 and conductors 170. In at least some embodiments, the control module 146 can drive the light source 152 to produce pulses of light with frequency, duration, and intensity programmed into the control module. In at least some embodiments, the control module 146 can be programmed to drive the light source 152 to produce different pulses of light which differ in one or more of frequency, duration, or intensity.

FIG. 2 illustrates an opposing end of the optical waveguide 154 with a light emission region 157. In some embodiments, there may be multiple light emission regions 157 along the optical waveguide 154 instead of, or in addition to, a light emission region at a tip of the optical waveguide 154, as illustrated in FIG. 2. In at least some embodiments, an emission region 157 can be formed by removal of the cladding 155 from the core 153 of the optical waveguide. Examples of light emission regions can be found in U.S. Patent Application Publication 2020/0155854, incorporated herein by reference in its entirety.

Figure 3:
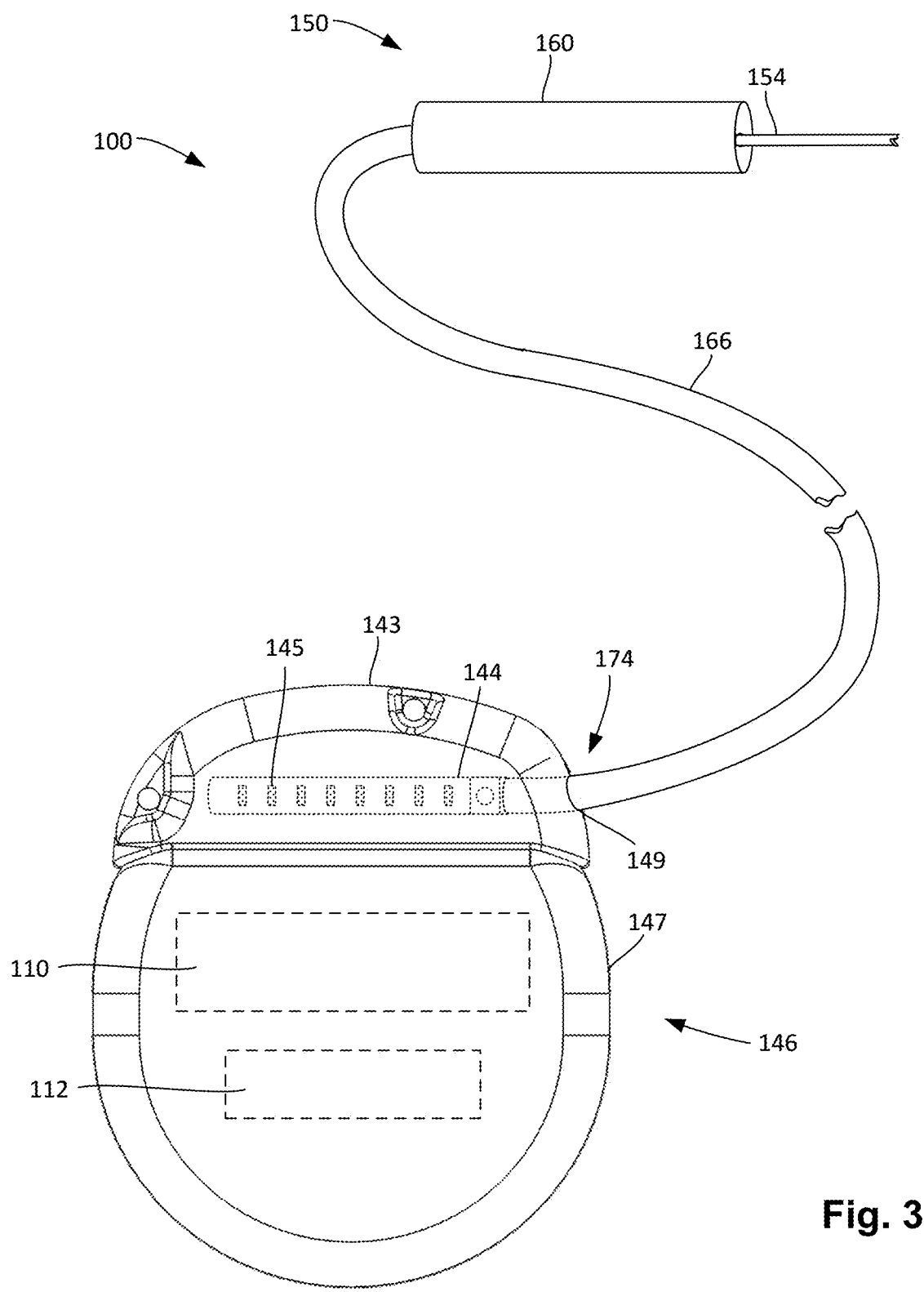
FIG. 3 is a schematic side view of one embodiment of a control module coupled to the implantable light generation arrangement of FIG. 1A.

FIG. 3 is a schematic side view of a portion of an embodiment of an optical or optical/electrical stimulation system 100. The stimulation system 100 includes the implantable arrangement 150 that is configured to couple one or more proximal ends 174 of the lead 166 to a control module 146. In FIG. 2, the lead 166 is shown coupled to a single port 149 defined in a control module connector 144.

The control module connector 144 defines at least one port 149 into which a proximal end 174 can be inserted. The control module 146 (or other device) can define any suitable number of ports including, for example, one, two, three, four, five, six, seven, eight, or more ports.

The control module connector 146 also includes connector contacts 145 disposed within each port 149. When the proximal end 174 is inserted into the port 149, the connector contacts 145 can be aligned with a plurality of terminals 168 (FIG. 1A) disposed along the proximal end(s) 174. Examples of connectors in control modules are found in, for example, U.S. Pat. Nos. 7,244,150 and 8,224,450, which are incorporated herein by reference in their entireties, as well as other references listed herein.

In at least some embodiments, the control module 146 includes a connector housing 143 (which is also often called a header) and a sealed electronics housing 147. In at least some embodiments, an electronic subassembly 110 and an optional power source 112 are disposed in the electronics housing 147. Other embodiments of a control module 146 may have more or fewer components.

The optional power source 112 can provide power to the electronic subassembly 110. The electronic subassembly 110 is, at least in some embodiments, programmable and is configured to direct the optical and, if present, electrical stimulation. The electronic subassembly 110 is electrically is coupled to the connector contacts 154 and controls the light source 152 through signals sent to the connector contacts 154 and through the terminals 168 and conductors 170 lead 166 to the light source.

Figure 5:
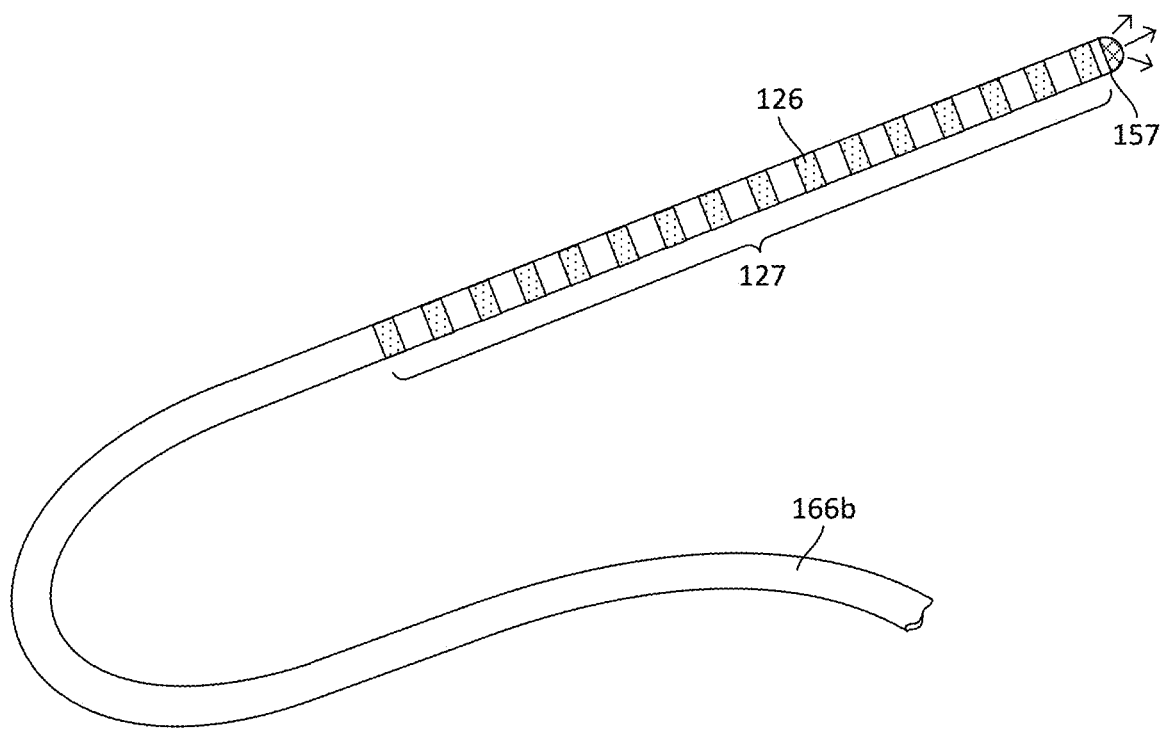
FIG. 5 is a schematic side view of one embodiment of a distal portion of the distal lead of FIG. 4 with electrodes and light emission regions.
Figure 4:
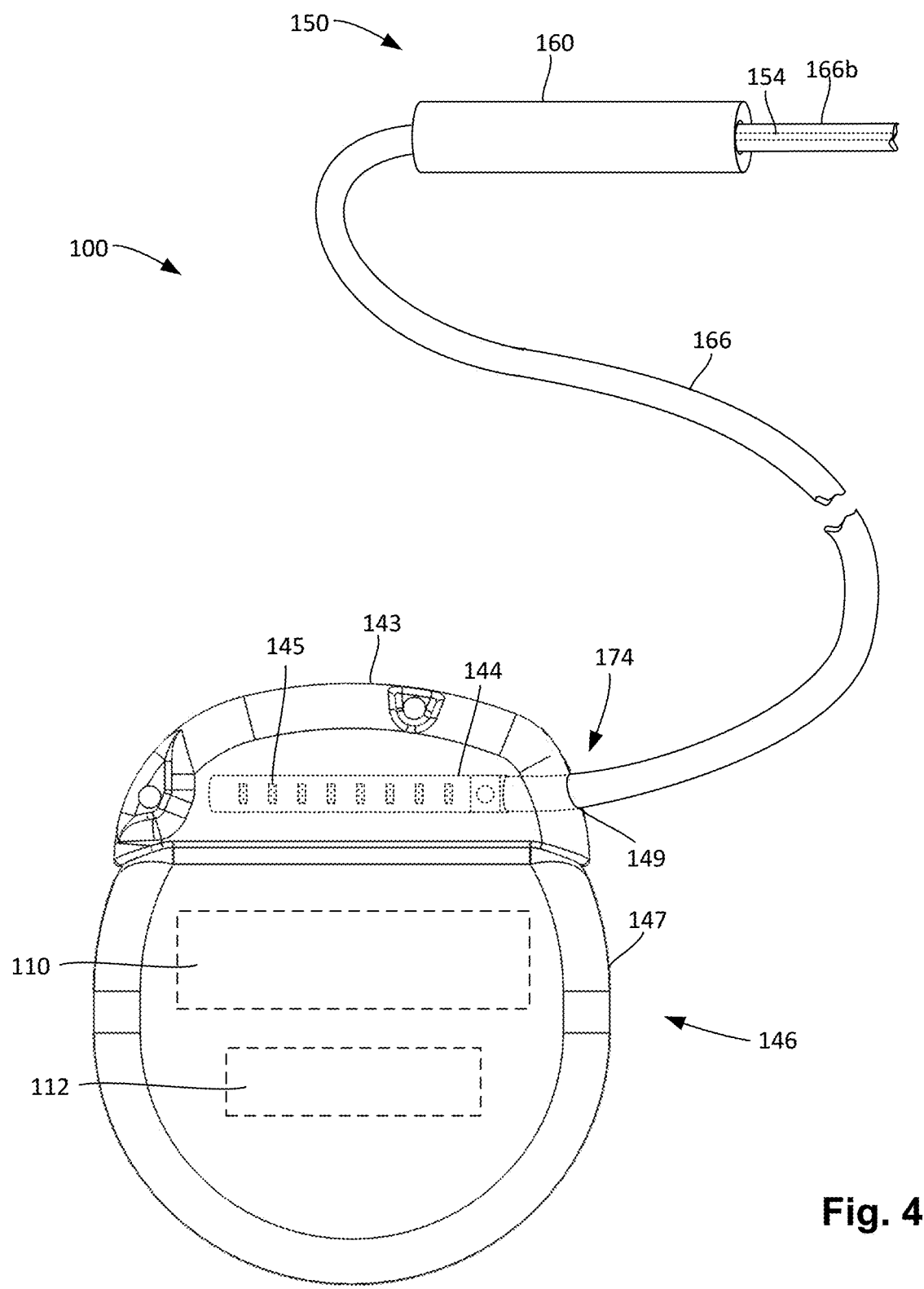
FIG. 4 is a schematic side view of one embodiment of a control module coupled to the implantable light generation arrangement having a distal lead for electrical stimulation.

In at least some embodiments, the system is an optical/electrical stimulation system 100. One embodiment of an optical/electrical stimulation system 100 is illustrated in FIGS. 4 and 5. In this embodiment, a distal lead 166b extends out of the casing 160 with the optical waveguide 154 disposed in the distal lead 166b, as illustrated in FIG. 4, and the distal lead includes electrodes 126 in an array 127, as illustrated in FIG. 5, to provide electrical stimulation. Conductors (not shown) extend from some of the terminals 168 (FIG. 1A) to the electrodes 126 (FIG. 5). For example, in at least some embodiments, these conductors can pass through (or around) the casing 160 between the lead 166 and the distal lead 166b. The electronic subassembly 110 of the control module 146 can provide electrical stimulation through the connector contacts 154, the terminals 168, and the conductors to the electrodes 126 of the lead 166 and distal lead 166b. Examples of leads with both optical waveguides/fibers and electrodes can be found in U.S. Patent Application Publication 2020/0155854, incorporated herein by reference in its entirety.

The electrodes 126 can be formed using any conductive, biocompatible material. Examples of suitable materials include metals, alloys, conductive polymers, conductive carbon, and the like, as well as combinations thereof. In at least some embodiments, one or more of the electrodes 126 are formed from one or more of: platinum, platinum iridium, palladium, palladium rhodium, or titanium. Any suitable number of electrodes 126 can be used. For example, there can be two, four, six, eight, ten, twelve, fourteen, sixteen, or more electrodes 126. As will be recognized, other numbers of electrodes 126 may also be used.

The electrodes 126 of the distal lead 166*b* and terminals 168 of the lead 166 are typically disposed in, or separated by, a non-conductive, biocompatible material such as, for example, silicone, polyurethane, polyetheretherketone ("PEEK"), epoxy, and the like or combinations thereof. The lead 166 and distal lead 166*b* may be formed in the desired shape by any process including, for example, molding (including injection molding), casting, and the like.

The electrically conductive wires ("conductors") may be embedded in the non-conductive material of the lead 166 or distal lead 166*b* or can be disposed in one or more lumens (not shown) extending along the lead 166 or distal lead 166*b*. In some embodiments, there is an individual lumen for each conductor. In other embodiments, two or more conductors extend through a lumen. In at least some embodiments, the distal lead 166*b* includes a lumen for the optical waveguide 154. There may also be one or more lumens (not shown) that open at, or near the proximal end of the lead 166 or distal lead 166*b*, for example, for inserting a stylet to facilitate placement of the lead 166 or distal lead 166*b* within a body of a patient. Additionally, there may be one or more lumens (not shown) that open at, or near, the distal end of the distal lead 166*b*, for example, for infusion of drugs or medication into the site of implantation. In at least one embodiment, the one or more lumens are flushed continually, or on a regular basis, with saline, epidural fluid, or the like. In at least some embodiments, the one or more lumens are permanently or removably sealable at the distal end.

Figure 6:
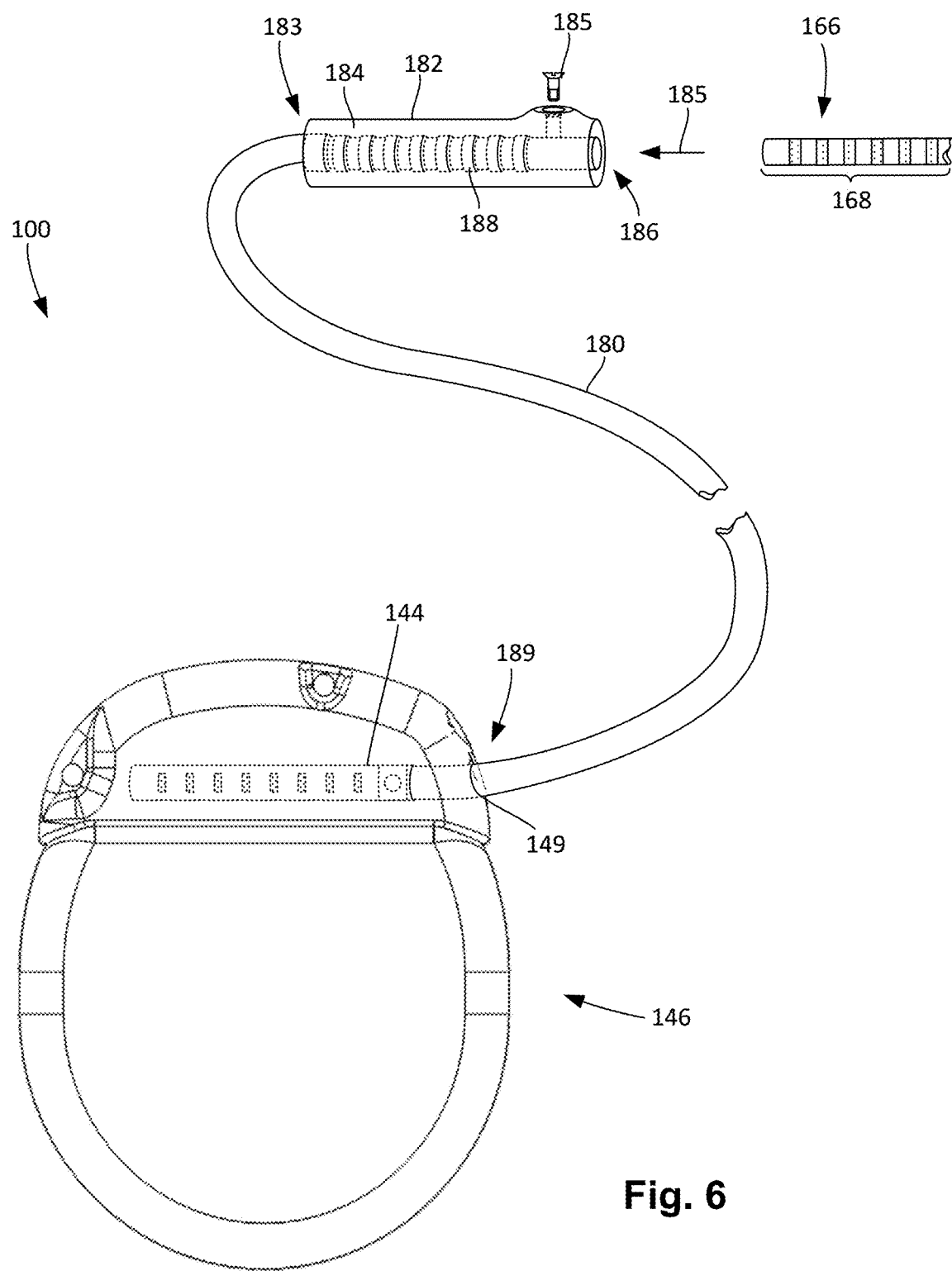
FIG. 6 is a schematic side view of one embodiment of a control module and lead extension for coupling to the implantable light generation arrangement of FIG. 1A.

FIG. 6 is a schematic side view of another embodiment of the optical or optical/electrical stimulation system 100. The optical or optical/electrical stimulation system 100 includes a lead extension 180 that is configured and arranged to couple one or more leads 166 to the control module 102. In FIG. 6, the lead extension 180 is shown coupled to a single port 149 defined in the control module connector 144.

A lead extension connector 182 is disposed on the lead extension 180. In FIG. 6, the lead extension connector 182 is shown disposed at a distal end 183 of the lead extension 180. The lead extension connector 182 includes a connector housing 184. The connector housing 184 defines at least one port 186 into which terminals 168 of the lead 166 can be inserted, as shown by directional arrow 185. The connector housing 184 also includes connector contacts 188. When the lead 166 is inserted into the port 186, the connector contacts 188 disposed in the connector housing 184 can be aligned with the terminals 168 of the 166.

In at least some embodiments, the proximal end 189 of the lead extension 180 is similarly configured and arranged as a proximal end of the lead 166. The lead extension 180 may include electrically conductive wires (not shown) that electrically couple the connector contacts 188 to a proximal end 189 of the lead extension 180 that is opposite to the distal end 183. The proximal end 189 of the lead extension 180 is configured for insertion into the control module connector 144. The lead extension connector 182 can include a fastener 185 that can be inserted into the connector housing 184 and fastened against the lead 166 to retain the lead within the lead extension connector.

Figure 7:
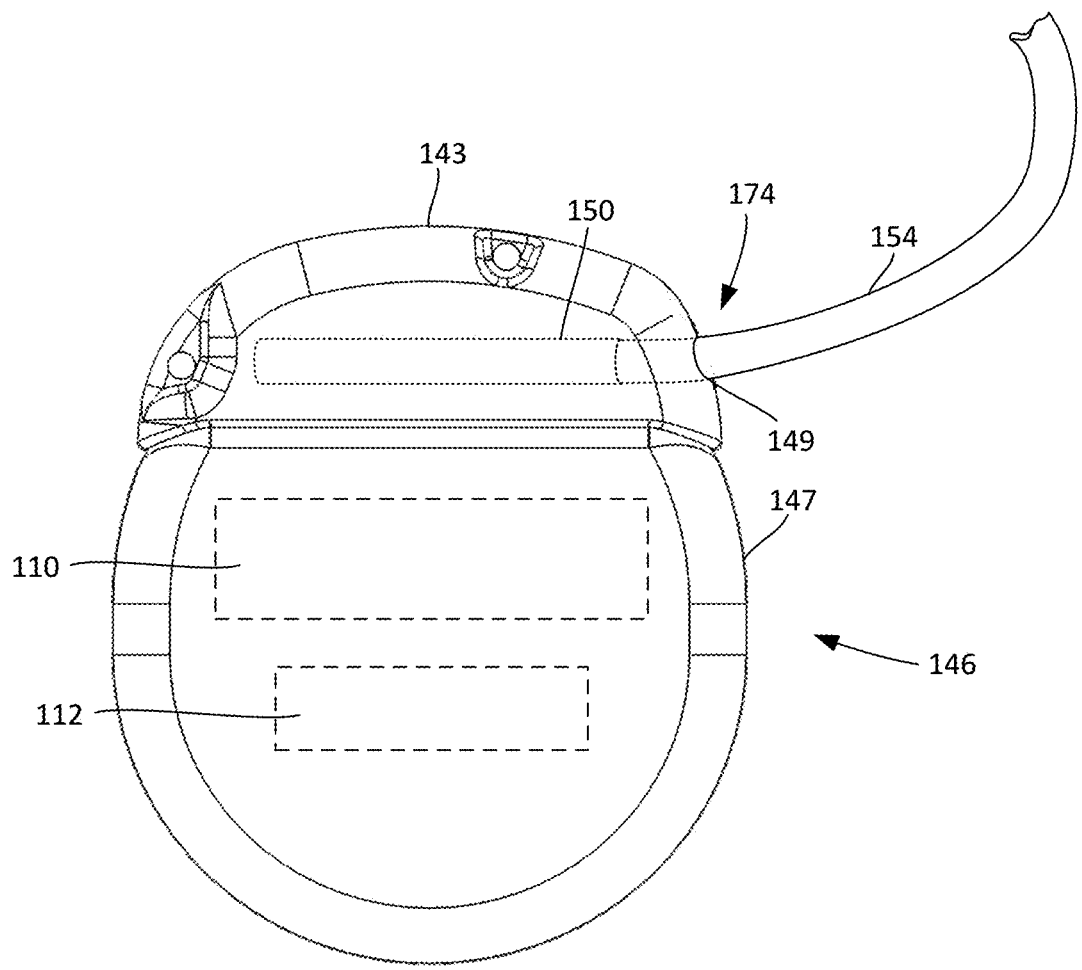
FIG. 7 is a schematic side view of one embodiment of a control module with an implantable light generation arrangement disposed in the control module.

FIG. 7 illustrates another embodiment in which the implantable arrangement 150 is disposed in the control module 146. The implantable arrangement 150 can be disposed in the connector housing 143, as illustrated in FIG. 7, or the sealed electronics housing 147. This implantable arrangement 150 does not include a lead 166, but rather the electronic subassembly 110 is electrically coupled to the light source 152 of the implantable arrangement to produce light pulses. The casing 160 may also be optional. The optical waveguide 154 extends out of the control module 146 to provide optical stimulation at the light emission region 157. In at least some embodiments, the optical waveguide 154 is removable from the control module 146 leaving the other components of the implantable arrangement 150 (for example, the light source 152, lens 156, and fixture 158 and, optionally, the casing 160) disposed in the control module 146. This embodiment can also be modified to provide both optical and electrical stimulation with the lead 166 of FIG. 5 (containing a portion of the optical waveguide 154) extending out of the control module 146.

Figure 8:
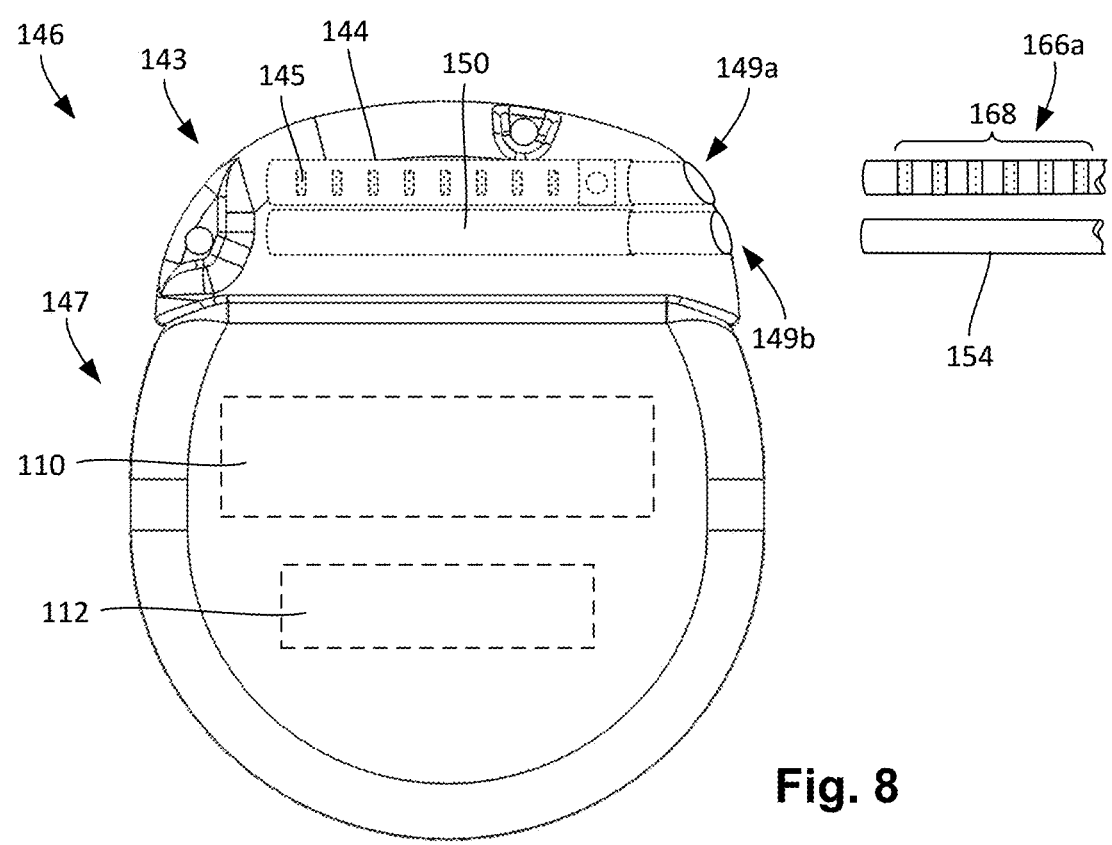
FIG. 8 is a schematic side view of another embodiment of a control module with an implantable light generation arrangement disposed in the control module, as well as a port for an electrical stimulation lead.

FIG. 8 illustrates another embodiment in which the implantable arrangement 150 is disposed in the control module 146. In this embodiment, the optical waveguide 154 extends from port 149*b*. In addition, an electrical stimulation lead 166*a* can be inserted into port 149*a*.

Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated herein by reference in their entireties.

Figure 9:
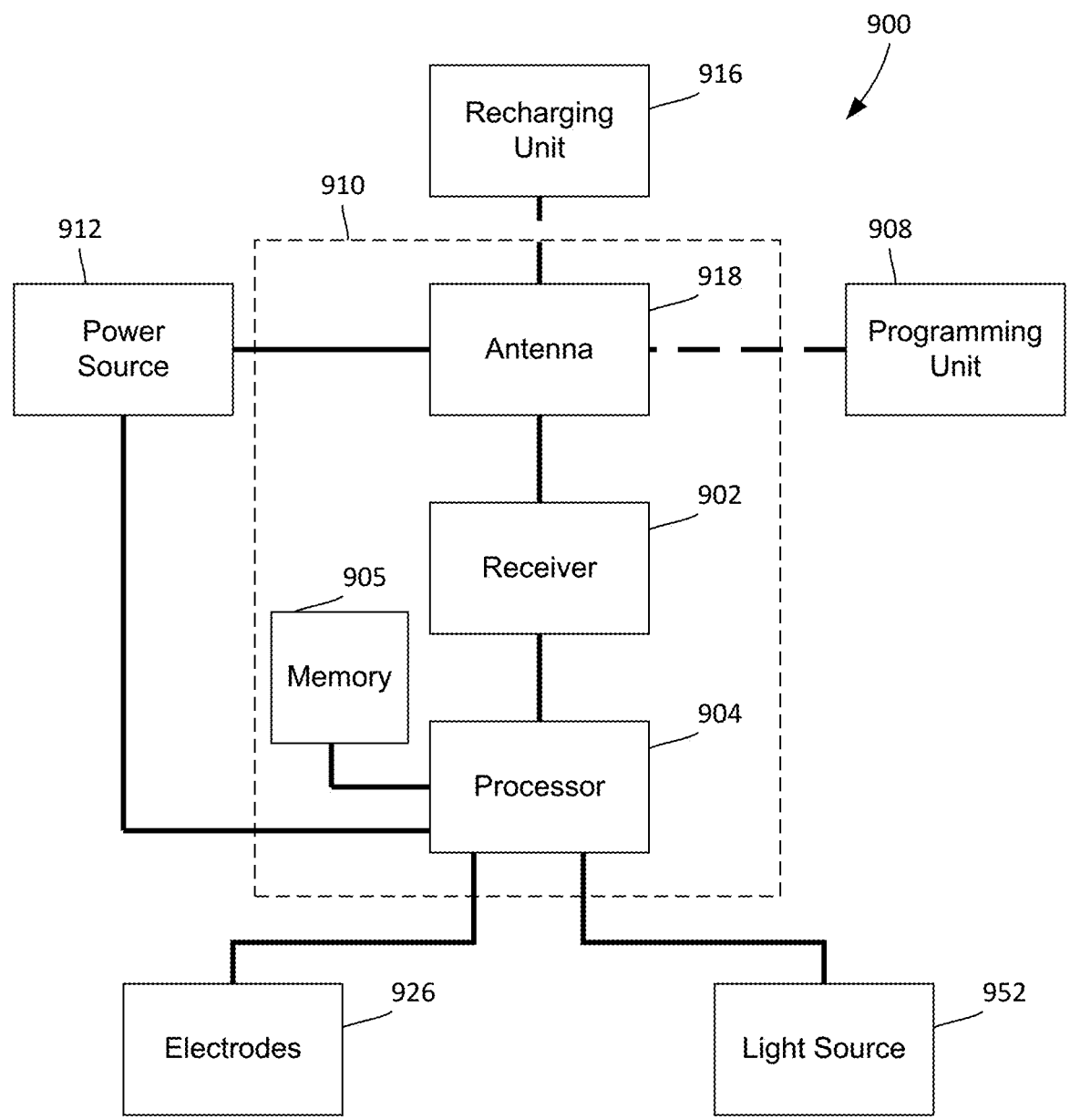
FIG. 9 is a block diagram of one embodiment of a system for optical or optical/electrical stimulation.

FIG. 9 is a schematic overview of one embodiment of components of an optical or optical/electrical stimulation system 900 including an electronic subassembly 910, such as electronic subassembly 110 above, disposed within a control module (for example, an implantable or external pulse generator). It will be understood that the optical or optical/electrical stimulation system can include more, fewer, or different components and can have a variety of different configurations including those configurations disclosed in the stimulator references cited herein.

In at least some embodiments, selected components (for example, a power source 912, an antenna 918, a receiver 902, a processor 904, and a memory 905) of the optical or optical/electrical stimulation system can be positioned on one or more circuit boards or similar carriers within a sealed housing of a control module. Any suitable processor 904 can be used and can be as simple as an electronic device that, for example, produces signals to direct or generate optical or optical/electrical stimulation at a regular interval or the processor can be capable of receiving and interpreting instructions from an external programming unit 908 that, for example, allows modification of stimulation parameters or characteristics.

The processor 904 is generally included to control the timing and other characteristics of the optical or optical/ electrical stimulation system. For example, the processor 904 can, if desired, control one or more of the timing, pulse frequency, amplitude, and duration of the optical or optical/electrical stimulation. In addition, the processor 904 can select one or more of the electrodes 926 to provide electrical stimulation, if desired. In some embodiments, the processor 904 selects which of the electrode(s) are cathodes and which electrode(s) are anodes.

Any suitable memory 905 can be used. The memory 905 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, magnetic storage devices, or any other medium which can be used to store the desired information and which can be accessed by a processor.

The processor 904 is coupled to a light source 952, such as a light source 152 as described above. Any suitable light source can be used including, but not limited to, LEDs, OLEDs, laser diodes, VCSELs, lamps, light bulbs, or the like or any combination thereof. In at least some embodiments, the optical or optical/electrical stimulation system may include multiple light sources. In at least some embodiments, each of the multiple light sources may emit light having a different wavelength or different wavelength range. Any suitable wavelength or wavelength range can be used including, but not limited to, visible, near infrared, and ultraviolet wavelengths or wavelength ranges. In at least some embodiments, the optical or optical/electrical stimulation system includes a light source that emits in the orange, red, or infrared wavelength ranges (for example, in the range of 600 to 1200 nm or the like.) In at least some embodiments, the optical stimulation system includes a light source that emits in the green or blue wavelength ranges (for example, in the range of 450 to 550 nm or the like.) A wavelength or wavelength range of a light source may be selected to obtain a specific therapeutic, chemical, or biological effect.

Any power source 912, such as power source 112 above, can be used including, for example, a battery such as a primary battery or a rechargeable battery. Examples of other power sources include super capacitors, nuclear or atomic batteries, fuel cells, mechanical resonators, infrared collectors, flexural powered energy sources, thermally-powered energy sources, bioenergy power sources, bioelectric cells, osmotic pressure pumps, and the like. As another alternative, power can be supplied by an external power source through inductive coupling via an antenna 918 or a secondary antenna. The external power source can be in a device that is mounted on the skin of the user or in a unit that is provided near the user on a permanent or periodic basis. In at least some embodiments, if the power source 912 is a rechargeable battery, the battery may be recharged using the antenna 918 and a recharging unit 916. In some embodiments, power can be provided to the battery for recharging by inductively coupling the battery to the external recharging unit 916.

In at least some embodiments, the processor 904 is coupled to a receiver 902 which, in turn, is coupled to an antenna 918. This allows the processor 904 to receive instructions from an external source, such as programming unit 908, to, for example, direct the stimulation parameters and characteristics. The signals sent to the processor 904 via the antenna 918 and the receiver 902 can be used to modify or otherwise direct the operation of the optical or optical/electrical stimulation system. For example, the signals may be used to modify the stimulation characteristics of the optical or optical/electrical stimulation system such as modifying one or more of stimulation frequency, stimulation duration, and stimulation amplitude/intensity. The signals may also direct the optical or optical/electrical stimulation system 900 to cease operation, to start operation, to start charging the battery, or to stop charging the battery. In other embodiments, the stimulation system does not include the antenna 918 or receiver 902 and the processor 904 operates as initially programmed.

In at least some embodiments, the antenna 918 is capable of receiving signals (e.g., RF signals) from an external programming unit 908 (such as a clinician programmer or patient remote control or any other device) which can be programmed by a user, a clinician, or other individual. The programming unit 908 can be any unit that can provide information or instructions to the optical or optical/electrical stimulation system 900. In at least some embodiments, the programming unit 908 can provide signals or information to the processor 904 via a wireless or wired connection. One example of a suitable programming unit is a clinician programmer or other computer operated by a clinician or other user to select, set, or program operational parameters for the stimulation. Another example of the programming unit 908 is a remote control such as, for example, a device that is worn on the skin of the user or can be carried by the user and can have a form similar to a pager, cellular phone, or remote control, if desired. In at least some embodiments, a remote control used by a patient may have fewer options or capabilities for altering stimulation parameters than a clinician programmer.

Optionally, the optical or optical/electrical stimulation system 900 may include a transmitter (not shown) coupled to the processor 904 and the antenna 918 for transmitting signals back to the programming unit 908 or another unit capable of receiving the signals. For example, the optical or optical/electrical stimulation system 900 may transmit signals indicating whether the optical or optical/electrical stimulation system 900 is operating properly or not or indicating when the battery needs to be charged or the level of charge remaining in the battery. The processor 904 may also be capable of transmitting information about the stimulation characteristics so that a user or clinician can determine or verify the characteristics.

Although the stimulation systems described above can provide both electrical stimulation and optical stimulation, it will be understood that the systems, arrangements, and methods described above can be modified to provide optical stimulation without electrical stimulation by, for example, may omitting, removing, or not employing the components, such as electrodes or elements that provide current to the electrodes, for electrical stimulation.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An implantable light generation arrangement for an optical or optical/electrical stimulation system, comprising:
   a light source having an emission surface, wherein the light source is configured to generate light and emit the light from the emission surface;

an optical waveguide having a first end and a core;
a ball lens disposed between the light source and the optical waveguide and configured to receive the light emitted from the light source and direct the light onto the core at the first end of the optical waveguide, wherein the ball lens is spaced apart from both the emission surface of the light source and the first end of the optical waveguide, wherein the ball lens has an index of refraction of at least 1.4 and a diameter of at least 1 mm, wherein the ball lens is spaced apart from the first end of the optical waveguide by an amount that is no more than half of the diameter of the ball lens; and
a fixture holding the light source, optical waveguide, and ball lens in a fixed arrangement.

2. The implantable light generation arrangement of claim 1, further comprising a casing surrounding the light source, a portion of the optical waveguide, the ball lens, and the fixture.

3. The implantable light generation arrangement of claim 1, further comprising a lead comprising terminals disposed along a proximal end of the lead and conductors coupled to the terminals and extending along the lead, wherein at least two of the conductors are coupled to the light source to electrically couple the light source to at least two of the terminals.

4. The implantable light generation arrangement of claim 1, wherein the diameter of the ball lens is at least five times as large as a diameter of the core of the optical waveguide.

5. The implantable light generation arrangement of claim 1, wherein the first end of the optical waveguide is spaced apart from the ball lens by a distance equal to a back focal length of the ball lens.

6. The implantable light generation arrangement of claim 1, wherein the emission surface of the light source is spaced apart from the ball lens by a distance of at least 0.16 mm.

7. A system for an optical or optical/electrical stimulation, comprising:
the implantable light generation arrangement of claim 1; and
a control module electrically coupleable to the light source of the implantable light generation arrangement.

8. An implantable light generation arrangement for an optical or optical/electrical stimulation system, comprising:
a light source having an emission surface, wherein the light source is configured to generate light and emit the light from the emission surface;
an optical waveguide having a first end and a core;
a ball lens disposed between the light source and the optical waveguide and configured to receive the light emitted from the light source and direct the light onto the core at the first end of the optical waveguide, wherein the ball lens has an index of refraction of at least 1.4 and a diameter of at least 1 mm, wherein the ball lens is spaced apart from the first end of the optical waveguide by an amount that is no more than half of the diameter of the ball lens;
a fixture holding the light source, optical waveguide, and ball lens in a fixed arrangement; and
a lead comprising terminals disposed along a proximal end of the lead and conductors coupled to the terminals and extending along the lead, wherein at least two of the conductors are coupled to the light source to electrically couple the light source to at least two of the terminals.

9. The implantable light generation arrangement of claim 8, further comprising a casing surrounding the light source, a portion of the optical waveguide, the ball lens, and the fixture, wherein another portion of the optical waveguide and at least a portion of the lead extend out of the casing.

10. The implantable light generation arrangement of claim 8, wherein the diameter of the ball lens is at least five times as large as a diameter of the core of the optical waveguide.

11. The implantable light generation arrangement of claim 8, wherein the first end of the optical waveguide is spaced apart from the ball lens by a distance equal to a back focal length of the ball lens.

12. The implantable light generation arrangement of claim 8, wherein the diameter of the ball lens is at least 4 mm.

13. A system for an optical or optical/electrical stimulation, comprising:
the implantable light generation arrangement of claim 8; and
a control module electrically coupleable to the light source of the implantable light generation arrangement.

14. An implantable light generation arrangement for an optical or optical/electrical stimulation system, comprising:
a light source having an emission surface, wherein the light source is configured to generate light and emit the light from the emission surface;
an optical waveguide having a first end and a core;
a ball lens disposed between the light source and the optical waveguide and configured to receive the light emitted from the light source and direct the light onto the core at the first end of the optical waveguide, wherein the ball lens has an index of refraction of at least 1.4 and a diameter of at least 1 mm, wherein the diameter of the ball lens is at least twice as large as a diameter of the emission surface of the light source, wherein the ball lens is spaced apart from the first end of the optical waveguide by an amount that is no more than half of the diameter of the ball lens; and
a fixture holding the light source, optical waveguide, and ball lens in a fixed arrangement.

15. The implantable light generation arrangement of claim 14, further comprising a casing surrounding the light source, a portion of the optical waveguide, the ball lens, and the fixture.

16. The implantable light generation arrangement of claim 14, further comprising a lead comprising terminals disposed along a distal end of the lead and conductors coupled to the terminals and extending along the lead, wherein at least two of the conductors are coupled to the light source to electrically couple the light source to at least two of the terminals.

17. The implantable light generation arrangement of claim 14, wherein the diameter of the ball lens is at least five times as large as a diameter of the core of the optical waveguide.

18. The implantable light generation arrangement of claim 14, wherein the first end of the optical waveguide is spaced apart from the ball lens by a distance of at least 0.5 mm.

19. The implantable light generation arrangement of claim 14, further comprising a lead comprising electrodes disposed along a distal end of the lead, wherein a portion of the optical waveguide extends along the lead.

20. A system for an optical or optical/electrical stimulation, comprising:
the implantable light generation arrangement of claim 14; and a control module electrically coupleable to the light source of the implantable light generation arrangement.

* * * * *